United States Patent [19]

Schmid et al.

[11] Patent Number: 5,468,406
[45] Date of Patent: Nov. 21, 1995

[54] MIXTURES OF ESTERS OF HIGHLY BRANCHED CARBOXYLIC ACIDS

[75] Inventors: Karl-Heinz Schmid, Mettmann; Frank Bongardt, Duesseldorf; Reinhold Wuest, Kaarst, all of Germany

[73] Assignee: Henkel Kommanditgesellschaft auf Aktien, Dusseldorf, Germany

[21] Appl. No.: 199,206

[22] PCT Filed: Aug. 20, 1992

[86] PCT No.: PCT/EP92/01903

§ 371 Date: Feb. 28, 1994

§ 102(e) Date: Feb. 28, 1994

[87] PCT Pub. No.: WO93/05009

PCT Pub. Date: Mar. 18, 1993

[30] Foreign Application Priority Data

Aug. 29, 1991 [DE] Germany ............... 41 28 646.4

[51] Int. Cl.$^6$ ................ C10M 105/34; C10M 105/38
[52] U.S. Cl. ........................... 252/56 S; 252/56 R
[58] Field of Search .................. 252/56 S, 56 R

[56] References Cited

U.S. PATENT DOCUMENTS

| | | | |
|---|---|---|---|
| 3,049,557 | 8/1962 | Emrick | 260/410.6 |
| 3,808,133 | 4/1974 | Brown | 252/56 R |
| 4,053,491 | 10/1977 | Koch et al. | 260/410.6 |
| 4,144,183 | 3/1979 | Koch et al. | 252/56 S |
| 4,234,497 | 11/1980 | Honig | 260/410.6 |
| 4,263,159 | 4/1981 | Berens et al. | 252/79 |
| 4,313,890 | 2/1982 | Chu et al. | 260/410.6 |
| 4,317,780 | 3/1982 | Mancini et al. | 252/56 S |

FOREIGN PATENT DOCUMENTS

| | | |
|---|---|---|
| 0010807 | 5/1980 | European Pat. Off. . |
| 9012849 | 11/1990 | WIPO . |

OTHER PUBLICATIONS

Methoden der organischen Chemie, Houben–Weyl, vol. E 5, Suppl.+following volumes to the 4th Edition, 1985, pp. 302–362.

E. F. Pratt, D. G. Kubler, J. Am. Chem. Soc. 76 (1954), pp. 52–56.

Ullmanns Encyklopaedie der Technischen Chemie, vol. 11, 4th Revised Edition, Verlag Chemie Weinheim, 1976, pp. 91 to 93.

*Primary Examiner*—Ellen M. McAvoy
*Attorney, Agent, or Firm*—Wayne C. Jaeschke; Norvell E. Wisdom, Jr.; Henry E. Millson, Jr.

[57] ABSTRACT

Described are mixtures of esters of carboxylic acids branched at the 2 position and polyol mixtures comprising 60 to 99.9% by weight of branched saturated aliphatic polyols with 2 to 6 primary hydroxy groups and 4 to 10 C atoms and 0.1 to 40% by weight of unbranched saturated aliphatic diols with 2 to 12 C atoms. In spite of the branched chain, such acids can be esterified very rapidly, the resulting esters being suitable for use as lubricants.

19 Claims, No Drawings

MIXTURES OF ESTERS OF HIGHLY BRANCHED CARBOXYLIC ACIDS

FIELD OF THE INVENTION

This invention relates to mixtures of esters of carboxylic acids branched in the 2-position with polyol mixtures which, in addition to branched, aliphatic, saturated $C_{4-10}$ polyols containing 2 to 6 primary hydroxyl groups, contain aliphatic, saturated, unbranched $C_{2-12}$ diols.

STATEMENT OF RELATED ART

Esters of carboxylic acids branched in the 2-position, such as 2-hexyldecanoic acid (isopalmitic acid), and of branched polyols containing 2 to 6 primary hydroxyl groups and 4 to 10 carbon atoms, are widely used as lubricants by virtue of their low-temperature behavior, flash point and viscosity behavior.

Thus, DE-A-23 03 918 describes lubricants containing isopalmitic acid esters of branched alcohols as sole constituents or in admixture with mineral oils and ester oils. Lubricants based on mineral oil and/or synthetic oils which contain polyol esters, such as pentaerythritol tetraisopalmitic acid ester, are known from DE-A-37 12 133. By virtue of their thermal stability, these polyol esters are suitable for the lifetime lubrication of heavily stressed engines, turbines, antifriction bearings and universal joints.

Esters of the type in question are conventionally produced by esterification using esterification catalysts, such as p-toluenesulfonic acid or tin grindings. Despite the esterification catalysts, the production of the isopalmitic acid ester of trimethylol propane on a laboratory scale takes, for example, 12 hours if a residual acid value below 1.5 and a residual hydroxyl value below 20 are to be achieved.

The problem addressed by the present invention was to provide new lubricants which would correspond in their physical properties to the esters of isopalmitic acid and branched polyols, but which could be produced in a shorter time.

SUMMARY OF THE INVENTION

It has now surprisingly been found that the esterification of branched carboxylic acids takes place very much more quickly with polyol mixtures of branched, aliphatic, saturated polyols and aliphatic, saturated unbranched diols and that the ester mixtures obtained show excellent properties as lubricants.

The present invention relates to ester mixtures of carboxylic acids branched in the 2-position corresponding to general formula (I):

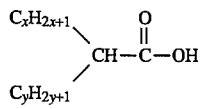

in which x and y may be the same or different and stand for a number of 4 to 22, with the proviso that x+y is an integer of 10 to 42, and polyol mixtures of a) 60 to 99.9% by weight of branched aliphatic saturated polyols containing 2 to 6 primary hydroxyl groups and 4 to 10 carbon atoms and b) 0.1 to 40% by weight of aliphatic, saturated, unbranched diols containing 2 to 12 carbon atoms (percentages by weight based on the polyol mixture).

DESCRIPTION OF PREFERRED EMBODIMENTS

The carboxylic acids highly branched in the 2-position can be obtained in various ways. Thus, corresponding carboxylic acids can be produced by introduction of carbon monoxide into organic molecules branched in the 2-position, such as alkanols or alkyl halides branched in the 2-position, in the presence of water and acidic catalysts (Koch-Haaf synthesis). The addition of carbon monoxide formula R—CH=CHR in the presence of water and nickel, cobalt, rhodium, ruthenium, palladium and platinum compounds also leads to corresponding carboxylic acids branched in the 2-position. Reviews of methods for producing these 2-carboxylic acids as known from organic chemistry can be found in *Methoden der organischen Chemie* [Title in English: Methods of Organic Chemistry], Houben-Weyl, Vol. E 5, Suppl.+ following volumes to the 4th Edition, 1985, pages 302-362. In addition, carboxylic acids such as these branched in the α-position to the carboxyl group can be obtained by oxidation of branched-chain alcohols from petroleum chemistry, for example by oxidation of an isomer mixture of branched-chain $C_{16}$ alcohols. Branched $C_{16}$ alcohols such as these may in turn be prepared by aldol condensation of isooctyl aldehyde which in turn can be prepared from isoheptane obtained in the cracking of petroleum. Another method is based on the oxidation of the α-branched primary alcohols obtained by the Guerbet method. In the Guerbet method, saturated primary alcohols are dimerized to defined α -branched primary alcohols by boiling in the presence of catalytic quantities of alkali metal hydroxide and heavy metal salts (cf. E. F. Pratt, D. G. Kubler, *J. Am. Chem. Soc.* 76 (1954), pages 52-56). For example, 2-hexyldecanol can be obtained from n-octanol by the Guerbet method and can be converted into isopalmitic acid by oxidation. Preferred branched carboxylic acids for the purposes of the invention are those for which x and y in general formula I are different and stand for a number of 4 to 22, with the proviso that x+y is a whole even number of 10 to 42. Examples of such carboxylic acids are 2-n-butyl-n-octanoic acid, 2-n-heptyl-n-undecanoic acid, 2-n-octyl-n-dodecanoic acid, 2-n-dodecyl-n-hexadecanoic acid and 2-n-hexadecyl-n-eicosanoic acid. Isopalmitic acid (2-n-hexyl-n-decanoic acid) prepared by oxidation of 2-hexyldecanol is most particularly preferred.

According to the invention, the ester mixtures are based on polyol mixtures which consist of 60 to 99.9% by weight and preferably of 80 to 95% by weight of branched aliphatic polyols containing 2 to 6 primary hydroxyl groups and 4 to 10 carbon atoms and of 0.1 to 40% by weight and preferably 5 to 20% by weight of aliphatic, saturated, unbranched diols containing 2 to 12 carbon atoms. The percentages by weight are all based on the polyol mixture, the sum total of the polyols having to be 100% by weight.

Of the branched, aliphatic saturated polyols, those containing tertiary carbon atoms (i.e. those containing no hydrogen atom) adjacent to the primary hydroxyl groups are preferred. Examples of such polyols are trimethylol ethane, trimethylol propane, trimethylol butane, pentaerythritol, neopentyl glycol, dipentaerythritol and/or mixtures thereof. Of these polyols, neopentyl glycol, trimethylol propane, pentaerythritol and/or dipentaerythritol are most particularly preferred.

The polyol mixture contains aliphatic, saturated unbranched diols containing 2 to 12 carbon atoms, preferably those containing two primary hydroxyl groups, more particularly α, ω-diols, such as butane-1,4-diol, pentane-1, 6-diol, hexane-1,6-diol and/or mixtures thereof, as a further constituent.

Ester mixtures of carboxylic acids branched in the 2-position and polyol mixtures of 60 to 99.9% by weight of trimethylol ethane, trimethylol propane, trimethylol butane, pentaerythritol, neopentyl glycol, dipentaerythritol and/or mixtures thereof and 0.1 to 40 by weight of butane- 1,4-diol, pentane- 1,5-diol, hexane- 1,6-diol and/or mixtures thereof are particularly suitable. Of these ester mixtures, those containing isopalmitic acid (2-n-hexyl-n-dodecanoic acid) as the highly branched carboxylic acid and 80 to 95% by weight of trimethylol propane, neopentyl glycol, pentaerythritol and/or dipentaerythritol and 5 to 20% by weight of butane-1,4-diol, pentane-1,5-diol, hexane-1,6-diol and/or mixtures thereof as the polyol mixture are particularly preferred.

The esterification of the carboxylic acids branched in the 2-position with the polyol mixture may be carried out under typical esterification conditions, for example as defined in *Ullmanns Encyklopädie der Technischen Chemie* [Title in English: Ullmann's Encyclopedia of Chemical Technology], Vol. 11, 4th Revised Edition (Verlag Chemie, Weinheim, 1976), pages 91 to 93. In general, the reactants are heated at temperatures of 160° to 260° C. in the presence of esterification catalysts, such as p-toluenesulfonic acid, tin grindings or tin compounds. The reaction products may optionally be aftertreated by washing with short-chain alcohols in order to free the esters obtained from any acid residues. Any excess acid may of course also be removed by washing out with alkalis. If desired, the ester mixtures according to the invention may be conventionally bleached after their production, for example by wet bleaching in the presence of aluminum silicate as the bleaching agent.

The ester mixtures according to the invention are prepared by complete or substantially complete esterification using conventional methods. Ester mixtures having a residual acid value below 1.5, more particularly below 1, and a residual hydroxyl value below 20 and more particularly below 10, which are obtained in an esterification time of less than 10 hours, are preferred.

The esters according to the invention are comparable in their flash point and in their good low-temperature and viscosity behavior with known esters based on the pure highly branched polyols.

EXAMPLES

Example 1 Preparation of trimethylol propane triisopalmitic acid ester 1,235.2 g of technical isopalmitic acid (97% by weight isopalmitic acid; acid value 210–220, saponification value (DIN 53401) 210–220, iodine value (DGF CV 11*b*)<1), 20.8 g of pentane-1,5-diol and 185.2 g of trimethylol propane were introduced into a reaction vessel and the moisture present was removed. 1.44 g of tin oxalate was then added as the esterification catalyst and the mixture was esterified under nitrogen for 8 hours at 180° to 240° C. A clear light yellow solution having an acid value (DIN 53402) of 1.05 was obtained. A clear yellow solution having an acid value of 0.28 was obtained by continued esterification of the reaction mixture for 30 minutes at 20° C./20 mbar and then for another 30 minutes at 2 mbar.

Comparison Example 203.2 g of trimethylol propane and 1,029.2 g of technical isopalmitic acid (see Example 1) were introduced into a reaction vessel with 1.23 g of tin oxalate and esterified under nitrogen for 8 hours at 190° to 240° C. A clear yellow liquid having an acid value of 3.17 was obtained. A solution having an acid value of 1.1 was obtained only after further esterification for another 4 hours at 240° C. When esterification was continued for 1 hour at 240° C./20 mbar, the solution obtained had an acid value of 0.77.

The invention claimed is:

1. Mixtures of esters of carboxylic acids corresponding to general formula (I):

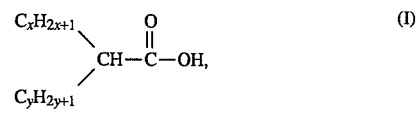

in which x and y may be the same or different and stand for a number of 4 to 22, with the proviso that x+y is an integer of 10 to 42, and polyol mixtures of
   a) 60 to 99.9% by weight of branched aliphatic saturated polyols containing 2 to 6 primary hydroxyl groups and 4 to 10 carbon atoms and
   b) 0.1 to 40% by weight of aliphatic, saturated, unbranched diols containing 2 to 12 carbon atoms, these percentages by weight being based on the polyol mixture .

2. Mixtures of esters as claimed in claim 1, wherein the branched carboxylic acids are selected from the group consisting of those corresponding to general formula (I) when x and y are different and stand for a number of 4 to 22, with the proviso that x+y is a whole even number in the range from 10 to 42.

3. Mixtures of esters as claimed in claim 2, wherein the highly branched carboxylic acid is 2-n-hexyl-n-decanoic acid.

4. Mixtures of esters as claimed in claim 3, wherein the polyol mixture consists of 80 to 95% by weight of polyols selected from the group consisting of branched, aliphatic, saturated polyols containing 2 to 6 primary hydroxyl groups and 4 to 10 carbon atoms and of 5 to 20% by weight of diols selected from the group consisting of aliphatic, saturated, unbranched diols containing 2 to 12 carbon atoms, these percentages by weight being based on the polyol mixture.

5. Mixtures of esters as claimed in claim 4, wherein the branched, aliphatic, saturated polyols are selected from the group consisting of trimethylol ethane, trimethylol propane, trimethylol butane, pentaerythritol, neopentyl glycol, dipentaerythritol and mixtures thereof.

6. Mixtures of esters as claimed in claim 5, wherein the unbranched diols are selected from the group consisting of butane-1,4-diol, pentane-1,5-diol, hexane-1,6-diol and mixtures thereof .

7. Mixtures of esters as claimed in claim 1, wherein the polyol mixture consists of 60 to 99.9% by weight of polyols selected from the group consisting of trimethylol ethane, trimethylol propane, trimethylol butane, pentaerythritol, neopentyl glycol, dipentaerythritol and mixtures thereof and of 0.1 to 40% by weight of diols selected from the group consisting of butane-1,4-diol, pentane-1,5-diol, hexane1,6-diol and mixtures thereof.

8. Mixtures of esters as claimed in claim 2, wherein the polyol mixture consists of 80 to 95% by weight of polyols selected from the group consisting of branched, aliphatic, saturated polyols containing 2 to 6 primary hydroxyl groups and 4 to 10 carbon atoms and of 5 to 20% by weight of diols selected from the group consisting of aliphatic, saturated, unbranched diols containing 2 to 12 carbon atoms, these percentages by weight being based on the polyol mixture.

9. Mixtures of esters as claimed in claim 1, wherein the polyol mixture consists of 80 to 95% by weight of polyols selected from the group consisting of branched, aliphatic, saturated polyols containing 2 to 6 primary hydroxyl groups and 4 to 10 carbon atoms and of 5 to 20% by weight of diols selected from the group consisting of aliphatic, saturated, unbranched diols containing 2 to 12 carbon atoms, these percentages by weight being based on the polyol mixture.

10. Mixtures of esters as claimed in claim 3, wherein the branched, aliphatic, saturated polyols are selected from the group consisting of trimethylol ethane, trimethylol propane, trimethylol butane, pentaerythritol, neopentyl glycol, dipentaerythritol and mixtures thereof.

11. Mixtures of esters as claimed in claim 2, wherein the branched, aliphatic, saturated polyols are selected from the group consisting of trimethylol ethane, trimethylol propane, trimethylol butane, pentaerythritol, neopentyl glycol, dipentaerythritol and mixtures thereof.

12. Mixtures of esters as claimed in claim 1, wherein the branched, aliphatic, saturated polyols are selected from the group consisting of trimethylol ethane, trimethylol propane, trimethylol butane, pentaerythritol, neopentyl glycol, dipentaerythritol and mixtures thereof.

13. Mixtures of esters as claimed in claim 10, wherein the unbranched diols are selected from the group consisting of butane-1,4-diol, pentane-1,5-diol, hexane-1,6-diol and mixtures thereof.

14. Mixtures of esters as claimed in claim 2, wherein the unbranched diols are selected from the group consisting of butane-1,4-diol, pentane-1,5-diol, hexane-1,6-diol and mixtures thereof.

15. Mixtures of esters as claimed in claim 1, wherein the unbranched diols are selected from the group consisting of butane-1,4-diol, pentane-1,5-diol, hexane-1,6-diol and mixtures thereof.

16. The mixtures of esters of claim 1 wherein the diols of component b) contain from 4 to 12 carbon atoms.

17. A process for the preparation of the mixture of esters of claim 1 comprising the steps of A) reacting at least one carboxylic acid of formula I

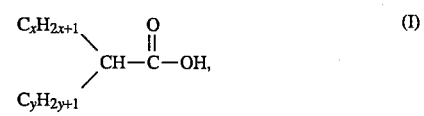

in which x and y may be the same or different and stand for a number of 4 to 22, with the proviso that x+y is an integer of 10 to 42, with a polyol mixture of
  a) from 60 to 99.9% by weight of at least one branched aliphatic saturated polyol containing 2 to 6 primary hydroxyl groups and 4 to 10 carbon atoms, and
  b) from 0.1 to 40% by weight of at least one aliphatic, saturated, unbranched diol containing 2 to 12 carbon atoms, wherein the above percentages are based on the polyol mixture, in the presence of an esterification catalyst, and B) isolating the mixture of esters of claim 1 from the reaction mixture.

18. The process of claim 17 wherein step A) is carried out at a temperature in the range of from 160° to 260° C.

19. The process of claim 17 wherein the mixture of esters has a residual acid value below 1.5.

* * * * *